United States Patent [19]

Herrmann et al.

[11] Patent Number: 5,455,357
[45] Date of Patent: Oct. 3, 1995

[54] SUBSTITUTED THIAZOLINE-DIOXETAN SUBSTRATES, PROCESS FOR THE PRODUCTION AND USE

[75] Inventors: Rupert Herrmann; Hans-Peter Josel; Christian Klein, all of Weilheim; Dieter Heindl, München, all of Germany

[73] Assignee: Boehringer Mannheim GmbH, Mannheim, Germany

[21] Appl. No.: 150,188

[22] PCT Filed: Mar. 29, 1993

[86] PCT No.: PCT/EP93/00752

§ 371 Date: Nov. 30, 1993

§ 102(e) Date: Nov. 30, 1993

[87] PCT Pub. No.: WO93/20083

PCT Pub. Date: Oct. 14, 1993

[30] Foreign Application Priority Data

Apr. 1, 1992 [DE] Germany ............ 42 10 759.8

[51] Int. Cl.⁶ .................................. C07D 513/10
[52] U.S. Cl. ........................................ 548/147
[58] Field of Search ................................. 548/147

[56] References Cited

U.S. PATENT DOCUMENTS

| | | |
|---|---|---|
| 4,857,652 | 8/1989 | Schaap . |
| 4,959,182 | 9/1990 | Schaap . |
| 4,962,192 | 10/1990 | Schaap . |
| 4,983,779 | 1/1991 | Schaap . |
| 5,004,565 | 4/1991 | Schapp . |
| 5,013,827 | 5/1991 | Schaap . |
| 5,068,339 | 11/1991 | Schaap et al. . |
| 5,089,630 | 2/1992 | Bronstein et al. . |

OTHER PUBLICATIONS

White, E. II., et al. (1980) Jour. Amer. Chem. Soc., 102:9, pp. 3199–3208.

*Primary Examiner*—Robert Gerstl
*Attorney, Agent, or Firm*—Felfe & Lynch

[57] ABSTRACT

Compounds of the general formula III,

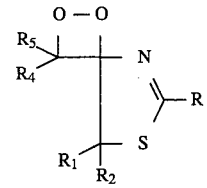

in which R represents

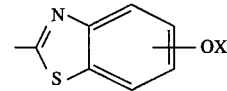

or

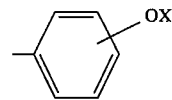

and in which $R_1$ and $R_2$ are the same or different and represent hydrogen or straight-chained or branched lower alkyl $C_1$–$C_6$, and X represents a cleavable group, at least one of the groups $R_4$ or $R_5$ represents a group that stabilizes the dioxetan structure and at most one of the groups $R_4$ or $R_5$ represents hydrogen. These compounds can be used as substrates in immunological assays and in DNA diagnostics using activating agents for the formation of colour.

8 Claims, No Drawings

SUBSTITUTED THIAZOLINE-DIOXETAN SUBSTRATES, PROCESS FOR THE PRODUCTION AND USE

This application is a 371 of PCT/EP93/00752 filed on Mar. 29, 1993.

The invention concerns thiazoline-dioxetan substrates, processes for the production and use in enzymatic analytical methods.

The reaction of luciferin (formula I) with luciferase, oxygen and ATP leads to the formation of oxiluciferin. In this reaction, light (maximum wavelength at 562 nm) is emitted as chemiluminescence. In this process the dioxetan of formula II is presumably formed as a high-energy intermediate (F. McCapra, Chem. Commun. 155 (1968)). Numerous chemiluminescing 1,2-dioxetan compounds have been developed on the basis of this postulate. The adamantyl residue has been described for the stabilization of the instable 1,2-dioxetans (EP-A 0 254 051, EP-A 0 352 713, WO 91/03479, WO 90/07511 as well as the publications which they cited). However, none of the known compounds is based on the activated intermediate stage of luciferin according to formula II as the parent substance, a thiazoline derivative.

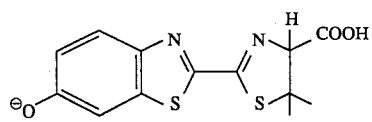

(I)

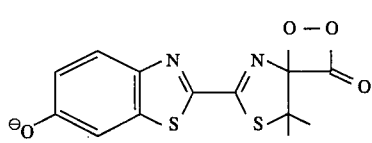

(II)

The object of the present invention was to provide a 1,2-dioxetan based on the activated intermediate stage of thiazolines and preferably of luciferin which is stable and only decomposes when reacted with an activating agent with formation of chemiluminescence. This object is achieved by a compound of the general formula III,

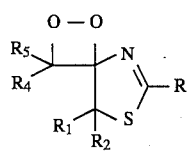

(III)

in which R is either

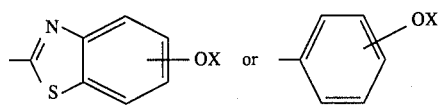

and $R_1$ and $R_2$ are in each case either the same or different and represent hydrogen or a lower alkyl $C_1-C_6$ which is straight-chained or branched, X is a cleavable group which can be cleaved by an activating agent and at least one of the groups $R_4$ or $R_5$ represents a group stabilizing the dioxetan structure and at most one of the groups $R_4$ or $R_5$ represents hydrogen.

Acids, bases, salts, enzymes, inorganic or organic catalysts and electron donors are preferably used as activating agents.

The group —O—X can be located at any position on the phenyl ring. However, if R is a benzthiazole group, the group —O—X is preferably situated at the 5 position. If R is a phenyl group, the group —O—X is preferably situated at the 3 position. This applies analogously for the —$OR_3$ group from which the —O—X group is formed.

—O—X is preferably the hydroxy salt of an oxy acid, phosphate, aryl- or alkylcarboxyl ester, alkyloxy or arylsilyloxy, sulfate, oxypyranoside.

The composition of the aryl and alkyl residues is not critical. Any person skilled in the art can select suitable residues for X without difficulty. It must merely be soluble and it must be possible to cleave X by activating agents.

$R_1$ and $R_2$ are preferably hydrogen, methyl or ethyl groups. If for example phosphate is used as —O—X, then the chemiluminescence reaction can be induced by addition of alkaline phosphatase. If the galactoside is used, the chemiluminescence reaction can be induced by β-galactosidase. If a silyloxy residue is used as —O—X, then the chemiluminescence can be induced by addition of fluoride.

Groups $R_4$ and/or $R_5$ are suitable for stabilizing the dioxetan structure that are those which protect the dioxetan group from reactions. This stabilization is preferably effected by steric screening of this group. Adamantanyl, phenyl, cyclohexyl, secondary and tertiary aliphatic alkyl groups (such as e.g. the t-butyl group) in a substituted and unsubstituted form are for example suitable. In this connection $R_4$ and $R_5$ can be the same or different. In the case of the adamantyl residue, this is preferably bound in such a way that $R_4$ and $R_5$ denote parts of the ring structure and are accordingly bridged (formula IIIa):

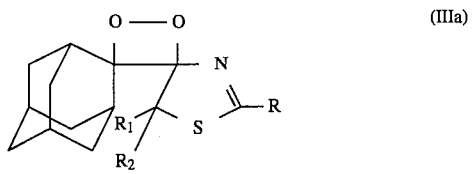

(IIIa)

The compounds of the general formula III are novel. A process for the synthesis of these compounds has not been previously known.

Accordingly the invention also concerns a process for the production of the compounds of formula III which is characterized in that a compound of formula IV or IVa

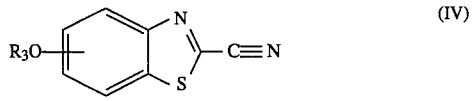

(IV)

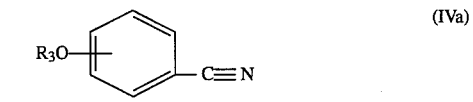

(IVa)

in which $R_3$ represents alkyl which is straight-chained or branched with 1–6 C-atoms and preferably methyl or ethyl is reacted with a compound of formula V

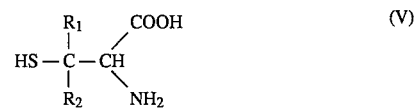

(V)

in which $R_1$ and $R_2$ have the aforementioned meanings, it is reacted with aldehydes or ketones in the presence of an alkyllithium compound while excluding water and air, the reaction product is decarboxylated, the alkoxy group is dealkylated, the chemically labile —O—X group is introduced at this position according to methods familiar to a person skilled in the art and it is photooxygenated to the dioxetan.

The reaction of the compound of formula IV (alkoxybenzthiazol-2-carboxylic acid nitrile) or IVa with the compound of formula V (preferably penicillamine or cysteine) is preferably carried out in a polar solvent such as water or water-alcohol mixtures at room temperature in the absence of light.

Compounds which are suitable as the aldehydes and ketones are those which, as residues $R_4$ and/or $R_5$, stabilize the dioxetan structure of compounds of formula III. Such a stabilization can be achieved by steric screening of the dioxetan structure. Suitable ketones and aldehydes are for example adamantanone, benzaldehyde, cyclohexanone, secondary and tertiary aliphatic aldehydes and ketones such as e.g. di-t-butylketone.

The introduction of $R_3$ is preferably carried out free from water in an aprotic organic solvent such as e.g. THF by reaction of the thiazoline-carboxylic acid obtained in this way with an aldehyde or ketone while excluding air and cooling. This is particularly preferably carried out at temperatures of $-50°$ to $-100°$ C. The alkyllithium compound is preferably added as a solution in a hydrocarbon (pentane, hexane). Butyllithium is particularly preferably used. After the reaction is completed, the compound obtained is precipitated from the reaction mixture, preferably by addition of an aqueous salt solution at room temperature.

Decarboxylation of the β-hydroxycarboxylic acid formed in this way in order to introduce a double bond is preferably carried out under dehydrating conditions e.g. with azodicarboxylic acid diethyl ester and triphenylphosphine.

It is expedient to carry out the dealkylation at the 6' position by addition of a dealkylation agent such as for example trimethyliodosilane. The process is preferably carried out free from water.

The thiazoline-carboxylic acid can likewise preferably be converted into a thiazolin-4-one via the intermediate amine and alcohol stage and afterwards converted into a thiazolin-4-thione by reaction with sulfide. This thiazolin-4-thione is reacted with a hydrazone of the aldehyde or ketone, preferably with adamantanone-2-hydrazone or benzaldehyde hydrazone which can contain a cleavable group (adamantanone tosylhydrazone or benzaldehyde tosylhydrazone) to form the compounds according to the invention of formula III.

In order to produce compounds of formula III in which $R_4$ and/or $R_5$ represent a phenyl residue, an aliphatic residue or cycloalkyl residue, a substituted 2-phenyl-5,5-dialkyl-thiazolin-4-one can also be converted in a Grignard reaction with subsequent introduction of a double bond at the 4 position of the thiazoline to the 4-substituted derivative. Subsequently the dioxetan group is introduced as described below.

The introduction of the chemically-labile group X is carried out according to methods familiar to a person skilled in the art. Such methods are for example described in Houben-Weyl XII/2 K. Sasse, P. 143 ff, Ed E. Müller, Thieme, Stuttgartt (1964).

It is expedient to introduce the dioxetan group by reacting the alkene derivative (double bond at the 2 position of the thiazoline) which is preferably dissolved in a polar organic solvent such as methylene chloride or chloroform at a temperature of $-100°$ to $50°$ C. and irradiating with visible light using a sensitizer (e.g. Rose Bengal, methylene blue, cf. Tetrahedron Letters (1988) 3137–3140).

For purification it is for example filtered. The supernatant contains the desired compound of formula III.

The invention in addition concerns a method for the determination of an acid, base, salt, enzyme, inorganic or organic catalyst and electron donor by reacting this compound with a compound of the general formula III and measuring the emitted light as a measure for the amount of the compound to be determined.

This method is particularly preferably used for the determination of enzymes, especially marker enzymes in immunological systems, or for DNA diagnostics with labelled DNA probes. Alkaline phosphatase is preferably determined in which case the chemically labile group X is phosphate or β-galactosidase in which case X=galactoside.

The invention is elucidated by the following examples.

It will be understood that the specification and examples serve to illustrate but do not limit the present invention since other embodiments within the spirit and scope of the invention will suggest themselves to those skilled in the art.

EXAMPLE 1

Synthesis of 2-(6'-methoxy-2'-benzthiazolyl)-5,5-dimethyl-$\Delta^2$ thiazoline-4-carboxylic acid (1)

2 g 6-methoxybenzthiazole-2-carboxylic acid nitrile is dissolved in ca. 100 ml methanol and a solution of 1.62 g penicillamine in 50 ml $H_2O$ is added. It is allowed to stir for 3 h at room temperature in the absence of light, the solution is subsequently acidified and filtered.

Yield: 1.3 g TLC: Rf (chloroform:methanol:acetic acid 9:1:0.1) 0.74

EXAMPLE 2

Synthesis of 2-(6'-methoxy-2'-benzthiazolyl)-5,5-dimethyl-4-(2'-hydroxy-2'-adamantyl$\Delta^2$-thiazoline-4-carboxylic acid (2):

A two-fold molar excess of butyllithium-hexane solution is added dropwise under nitrogen at $-78°$ C. to 1 g of compound (1) dissolved in ca. 100 ml dry THF and stirred for 1 hour. Subsequently the corresponding amount of 2-adamantanone dissolved in THF is added to this at $-78°$ C., it is stirred for 3 hours at $-78°$ C. and afterwards the reaction mixture is added to 100 ml of a saturated aqueous sodium chloride solution containing 20 mmol HCl.

The residue is recrystallized from chloroform/ether.

Yield: 0.5 g

EXAMPLE 3

Synthesis of 2-(6'methoxy-2'-benzthiazolyl)-5,5-dimethyl-4-(2'-adamantanylidene)$\Delta^2$-thiazoline (3)

Decarboxylation of the beta-hydroxycarboxylic acid and introduction of the double bond is achieved by reaction with equimolar amounts of $P(CC_6H_5)_3$ and azodicarboxylic acid-diethyl ester in THF at room temperature (see e.g. Mulzer, "Angew. Chemie 1977).

Synthesis of
2-(6'-hydroxy-2-benzthiazolyl)-5,5-dimethyl-4-
(2'adamantanylidene)$\Delta^2$-thiazoline (4)

1 g of compound (3) is dissolved in 10 ml dry CHCl3 and a 50% excess of trimethyliodosilane is added It is heated for 48 hours to ca. 70° C., methanol is added to the reaction mixture and the solution is rotary evaporated.

The residue is taken up in ethyl acetate and shaken out with 5% NaHCO$_3$ solution, dried and concentrated in a vacuum.

Yield: 0.25 g

EXAMPLE 4

Synthesis of
2-(6'-phosphoryl-2'-benzthiazolyl)-5,5-dimethyl-4-
(2'-adamantanylidene)$\Delta^2$-thiazoline (5)

Phosphorylation of (4) is accomplished using the usual literature methods. See e.g. Houben-Weyl XII/2 K. Sasse, P. 143 ff, Ed E. Müller, Thieme Stuttgartt (1964).

EXAMPLE 5

Synthesis of 1
[2'-(6"-phosphoryl-2"-benzthiazolyl)-5',5'-dimethyl-$\Delta^2$-thiazolinyl-]-2-(2"-spiroadamantyl)-dioxetan (6)

In order to photooxygenate (5), 10 mg of the alkene dissolved in 10 ml methylene chloride, to which immobilized Rose Bengal (Polyscience) is added, is irradiated for 1 hour at −78° C. with a 1000 watt lamp. The reaction proceeds quantitatively. The sensitizer Rose Bengal can be easily removed by filtration.

EXAMPLE 6

2-alkoxyphenyl-5,5-dimethyl-thiazoline-4-carboxylic acid It is produced analogously to Chem. Ztg. 1987, 111, 357.

33.5 mmol penicillamine, 33.5 mmol alkoxynitrile and 16.7 mmol potassium carbonate were heated to boiling in a mixture of 50 ml methanol containing 25 ml water for 12 hours under reflux. After cooling it is evaporated to one half in a vacuum. The mixture was washed once with 50 ml ether. The separated aqueous phase was adjusted to pH 4 with concentrated hydrochloric acid. In this process a pale yellow precipitate is formed, which was aspirated, washed once with a little water and dried at 60° C. in a vacuum.

Yield: 50–60%

EXAMPLE 7

2-alkoxyphenyl-5,5-dimethyl-thiazoline-4-carboxylic acid amide 4 mmol oxalyl chloride was added at 0° C. to a suspension of 4 mmol alkoxyphenyl-thiazoline carboxylic acid in 10 ml methylene chloride. After 30 minutes stirring at this temperature, a gentle stream of ammonia was passed in for 5 min at −20° C. After heating to room temperature, the suspension was diluted with 20 ml methylene chloride. The mixture was washed once with 10 ml 1N sodium hydroxide solution and subsequently washed twice with 20 ml water. The organic phase was dried over sodium sulfate. After the solvent had been removed by distillation an oil remained which was recrystallized from a small amount of ethyl acetate (yield: 60–80 %).

EXAMPLE 8

4-amino-2-alkoxyphenyl-5,5-dimethyl-thiazoline 4.8 mmol bromine was dissolved at 0° C. in 8 ml 3N sodium hydroxide solution. 4.4 mmol 2-alkoxyphenyl-5,5-dimethyl-thiazoline carboxylic acid amide was added to this mixture at 0° C. and stirred for 30 min at this temperature and for 20 min at 70° C. After dilution with 20 ml water, it is extracted by shaking with 40 ml ethyl acetate. The organic phase was washed twice with 15 ml water each time and dried over sodium sulfate. After the solvent had been removed by distillation an oil remained which was recrystallized from ethanol/water 1:1 (yield: 70–85%).

EXAMPLE 9

4-hydroxy-2-alkoxyphenyl-5,5-dimethyl-thiazoline 15 mmol sodium nitrite was added to a solution of 14.5 mmol amino-2-alkoxyphenyl-5,5-dimethyl-thiazoline in 32 ml half-concentrated hydrochloric acid at 0° C. and stirred for 20 min at this temperature. After neutralization with 3N sodium hydroxide solution, it was shaken out twice with 30 ml ethyl acetate each time. The organic phase was washed once with 20 ml water and dried over sodium sulfate. After the solvent had been removed by distillation an oil remained which was separated by column chromatography (silica gel, ethyl acetate/petroleum ether 1:1) (yield 75–80%).

EXAMPLE 10

2-alkoxyphenyl-5,5-dimethyl-thiazolin-4-one 11 mmol 4-hydroxy-2-alkoxyphenyl-5,5-dimethyl-thiazoline and 34 mmol cycloheptanone were dissolved in 160 ml toluene. After 40 ml toluene had been removed by distillation, 9 mmol aluminium triisopropylate was added and the mixture was heated to boiling for 3 hours under reflux. After cooling to room temperature, 100 ml ethyl acetate was added and the mixture was washed twice with 50 ml water each time. The combined aqueous phases were extracted once with 50 ml ethyl acetate. After drying the combined organic phases over sodium sulfate, the solvent was removed by distillation. The thiazolinone was separated from the remaining oil by column chromatography (silica gel, ethyl acetate/petroleum ether 1:4).

EXAMPLE 11

2-alkoxyphenyl-5,5-dimethyl-thiazolin-4-thione 5 mmol 2-alkoxyphenyl-5,5-dimethyl-thiazolin-4-one and 11 mmol 2,4-(4-bis-methoxyphenyl)-1,3-dithia-2,4-diphosphetan-2,4-disulfide were heated to boiling in 10 ml toluene for 8 hours under reflux. After cooling, the reaction mixture was separated by column chromatography (silica gel, ethyl acetate/petroleum ether 1:6) (yield: 30–40 %)

EXAMPLE 12

Adamantane-2-tosyl hydrazone 3.4 mmol tosyl hydrazide and 3.3 mmol adamantanone and one drop of concentrated sulphuric acid were heated to boiling in 10 ml ethanol for 4 hours under reflux. After cooling to room temperature it is evaporated to a volume of 1 ml in a vacuum. It was diluted with 20 ml water and neutralized with 2N sodium hydroxide solution. The mixture was shaken out twice with 20 ml ethyl acetate each time. The combined organic phases were washed once with 20 ml water and subsequently dried over sodium sulfate. The solution was concentrated evaporated down to a volume of 4 ml and allowed to stand for 15 hours at 4° C. Colourless needles precipitated (yield: 40%).

EXAMPLE 13

4-(2'-adamantanylidene-alkoxyphenyl-5,5-dimethylthiazoline 2 mmol adamantantosyl hydrazone was added to 10 ml of a methanolic 0.2M sodium methylate solution and this was then diluted with 20 ml diglyme. After the methanol had been removed by distillation it was heated to 120° C. until tosyl hydrazone was no longer detectable in TLC. 2 mmol of the 2-alkoxyphenyl-5,5-dimethyl-thiazolin-4-thions was added at this temperature and stirred for 15 minutes. Then 1 g copper powder was added and the mixture was stirred for a further 20 minutes at 150° C. After cooling, 100 ml water was added and the mixture was extracted three times with 50 ml ethyl acetate each time. The combined organic phases were washed once with 30 ml water and subsequently dried over sodium sulfate. After the solvent had been removed by distillation, an oil remained which was separated by column chromatography (silica gel, ethyl acetate/petroleum ether 1:6) (yield 20%).

EXAMPLE 14

4-benzyl-4-hydroxy-alkoxyphenyl-5,5-dimethyl-thiazoline 5 mmol 2-alkoxyphenyl-5,5-dimethyl-thiazolin-4-one (example 10) was added to 50 ml of an ethereal 0.2M benzyl magnesium chloride solution and the mixture was heated to boiling for 8 hours under reflux. After adding 20 ml water, the organic phase was separated, washed once with 20 ml water and subsequently dried over sodium sulfate. After removing the solvent by distillation an oil remained which is separated by column chromatography (silica gel; ethyl acetate/petroleum ether 1:5) (yield 30%).

EXAMPLE 15

4-benzylidene-alkoxyphenyl-5,5-dimethyl-thiazoline

A solution of 2 mmol 4-benzyl-4-hydroxy-alkoxyphenyl-5,5-dimethyl-thiazoline (example 14) in 20 ml ethyl acetate was shaken for 5 minutes with 20 ml half-concentrated hydrochloric acid. After neutralization with 2N sodium hydoxide solution, the organic phase was separated, washed once with 20 ml water and subsequently dried over sodium sulfate. After removing the solvent by distillation an oil remained which was separated by column chromatography (silica gel, ethyl acetate, petroleum ether 1:4) (yield 60%)

We claim:

1. A compound of formula III,

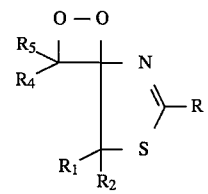

wherein R is

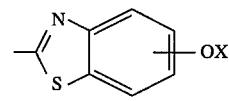

or

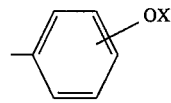

and wherein $R_1$ and $R_2$ are the same or different and are hydrogen or a straight chained or branched $C_1$–$C_6$ alkyl, X is a cleavable group and at least one of $R_4$ or $R_5$ is a group stabilizing the dioxetan structure selected from the group consisting of adamantyl, phenyl, cyclohexyl and a secondary or tertiary alkyl residue or wherein one of $R_4$ or $R_5$ is hydrogen.

2. The compound of claim 1 wherein O—X is at the 5 position when R is a benzthiazole group and wherein O—X is at the 3 position when R is phenyl.

3. The compound of claim 1 wherein $R_1$ and $R_2$ are H, methyl or ethyl.

4. The compound of claim 1 wherein O—X is selected from the group consisting of an hydroxy salt of an oxy acid, aryl-or alkylcarboxyl ester, alkyloxy, sulfate, arylsilyloxy and oxypyranoside.

5. The compound of claim 1 wherein O—X is phosphate, galactoside or silyloxy.

6. A compound of formula

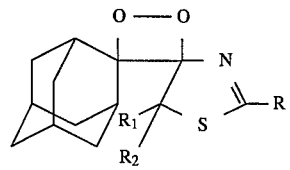

wherein R is

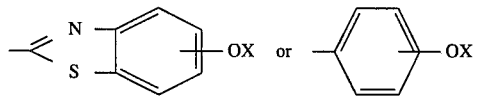

wherein X is a cleavable group and $R_1$ and $R_2$ are the same or different, and are hydrogen or a straight chained or branched $C_1$–$C_6$ alkyl.

7. A 4-(2'-adamantylidene)-alkoxyphenyl-5,5-dimethyl-thiazoline compound.

8. A 4-benzyl-4-hydroxy-alkoxyphenyl-5,5-dimethylthiazoline compound.

* * * * *